United States Patent
Edionwe

(10) Patent No.: US 12,226,110 B1
(45) Date of Patent: Feb. 18, 2025

(54) NEUROMONITORING SURGICAL DEVICE FOR BONE AND TISSUE REMOVAL

(71) Applicant: Joel Edionwe, San Antonio, TX (US)

(72) Inventor: Joel Edionwe, San Antonio, TX (US)

( * ) Notice: Subject to any disclaimer, the term of this patent is extended or adjusted under 35 U.S.C. 154(b) by 0 days.

(21) Appl. No.: 18/801,048

(22) Filed: Aug. 12, 2024

Related U.S. Application Data

(60) Provisional application No. 63/519,174, filed on Aug. 11, 2023.

(51) Int. Cl.
*A61B 17/16* (2006.01)
*A61B 17/00* (2006.01)

(52) U.S. Cl.
CPC *A61B 17/1671* (2013.01); *A61B 2017/00039* (2013.01); *A61B 2017/00128* (2013.01); *A61B 2017/0023* (2013.01); *A61B 2017/00367* (2013.01)

(58) Field of Classification Search
CPC ............ A61B 17/32; A61B 17/320016; A61B 17/320092; A61B 2017/320098; A61B 17/1604; A61B 17/1606; A61B 17/1608; A61B 17/1611
See application file for complete search history.

(56) References Cited

U.S. PATENT DOCUMENTS

| | | | |
|---|---|---|---|
| 5,775,331 A | 7/1998 | Raymond et al. | |
| 7,236,832 B2 | 6/2007 | Hemmerling et al. | |
| 9,084,551 B2 | 7/2015 | Brunnett et al. | |
| 10,398,459 B2 * | 9/2019 | Ferro | A61B 17/1608 |
| 11,166,716 B2 * | 11/2021 | Shelton, IV | A61B 17/34 |
| 11,793,447 B2 * | 10/2023 | Gharib | A61B 5/7475 |
| 2010/0010334 A1 * | 1/2010 | Bleich | A61B 17/1757 |
| | | | 606/108 |

OTHER PUBLICATIONS

TSI Tedan Surgical Innovations, Bayoneted CleanWave Kerrisons, Retrieved From Internet, Retrieved on Aug. 12, 2024, <URL: https://tedansurgical.com/bay-kerrison-4-mm-bite-40-deg-up-10-mm-open-160-mm-6-wrklength-228-mm-9-tialn-coated-black>.
Weinberg, Douglas S., et al., Cervical laminoplasty: indication, technique, complications, Journal of Spine Surgery, Mar. 30, 2020, vol. 6, No. 1, doi: 10.21037/jss.2020.01.05.

* cited by examiner

*Primary Examiner* — Anu Ramana

(57) ABSTRACT

A neuromonitoring surgical device for bone and tissue removal is a device that is designed for spinal decompression procedures to enable the removal of bone or tissue while enabling the user to monitor the tissue being grasped with the device. The device includes a bone-and-tissue remover, a first tissue probe, a first light indicator, a cable connector, and a monitoring device. The bone-and-tissue remover is designed to enable the minimal invasive removal of bone and/or tissue during the spinal decompression procedure. The first tissue probe enables the automatic detection of neural tissue grasped by the bone-and-tissue remover. The first light indicator directly alerts the user when neural tissue has been grasped by the bone-and-tissue remover. The cable connector enables the electrical and electronic connection of the bone-and-tissue remover to the monitoring device. The monitoring device allows the monitoring of the operation of the first tissue probe during the surgical procedure.

20 Claims, 8 Drawing Sheets

NEUROMONITORING SURGICAL DEVICE FOR BONE AND TISSUE REMOVAL

FIELD OF THE INVENTION

The present invention relates generally to surgical devices and neuromonitoring systems. More specifically, the present invention discloses a surgical device capable of removing bone and tissue with neuromonitoring capabilities that alert the user when neural tissue has been grasped by the surgical device.

BACKGROUND OF THE INVENTION

Nowadays, various surgical devices have been made available to help surgeons and medical professionals perform several medical procedures. For cervical, thoracic and lumbar spinal procedures and neuropediatric procedures, different surgical devices have been developed that help the user to accurately remove small portions of bone and/or soft tissue. Such surgical devices include, but are not limited to, Kerrison Rongeurs that are commonly utilized for decompression surgery. Kerrison Rongeurs enable the user to perform precise surgical procedures in a minimally invasive manner. However, the devices currently available have many disadvantages. For example, these devices provide no feedback to the user of what bone or tissue is being grasped by the device, which could be dangerous if the user accidentally resects neural tissue. To avoid this, different neuromonitoring systems and devices have been made available to be used during the surgery. However, utilizing several tools during the surgery procedure can be cumbersome and dangerous. Therefore, there is a need for a surgical device capable of removing bone and tissue with neuromonitoring capabilities.

An objective of the present invention is to provide a neuromonitoring surgical device for bone and tissue removal that includes integrated means to monitor tissue being grasped by the device. The present invention implements neuromonitoring means to prevent accidental resection of neural tissue without having to use external monitoring systems. Another objective of the present invention is to provide a neuromonitoring surgical device that can be manually operated and that can be disposed of after use.

Another objective of the present invention is to provide a neuromonitoring surgical device that can be connected to a separate monitoring device to monitor the signals generated by the neuromonitoring surgical device. Additional features and benefits of the present invention are further discussed in the sections below.

SUMMARY OF THE INVENTION

The present invention discloses a neuromonitoring surgical device for bone and tissue removal. The present invention is designed for spinal decompression procedures that involve removing tissue, ligaments, bone, etc., to free the spinal cord and nerve roots. Simultaneously, the present invention detects neural tissues being grasped by the device so that the surgeon is aware of accidental resection of neural tissue. The present invention is similar to the Kerrison Rongeurs but equipped with neuromonitoring means to help the user detect neural tissue while performing the procedure.

Further, the present invention is designed to be connected to a monitoring device from which the user can monitor the signals generated by the neuromonitoring surgical device to help the user keep track of the tissue being grasped with the device. The monitoring device can also provide the power necessary for the operation of the neuromonitoring surgical device. Furthermore, several features can be implemented into the neuromonitoring surgical device to alert the user of the tissue being grasped with the device. Additional features can be implemented to help improve the functionality of the present invention.

DETAIL DESCRIPTIONS OF THE INVENTION

Figure 1:
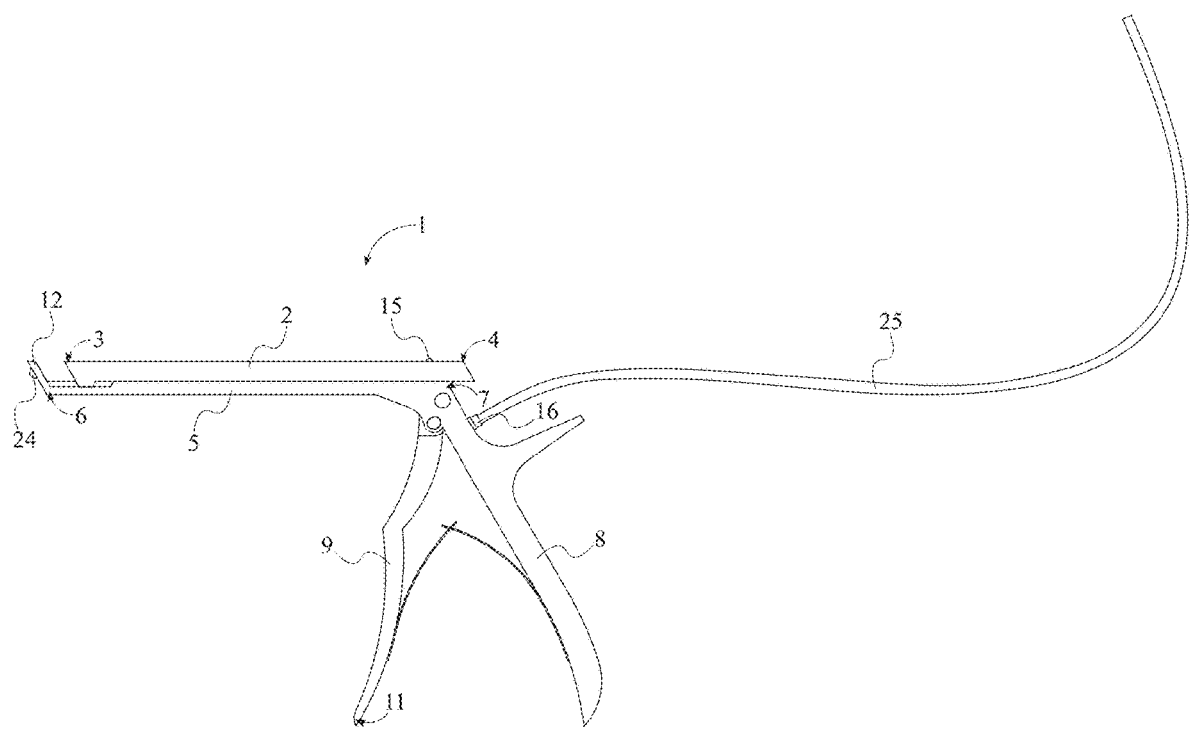
FIG. 1 is a side schematic view of the present invention, wherein the disposable power-and-data cable is shown coupled to the bone-and-tissue remover of the present invention.
Figure 2:
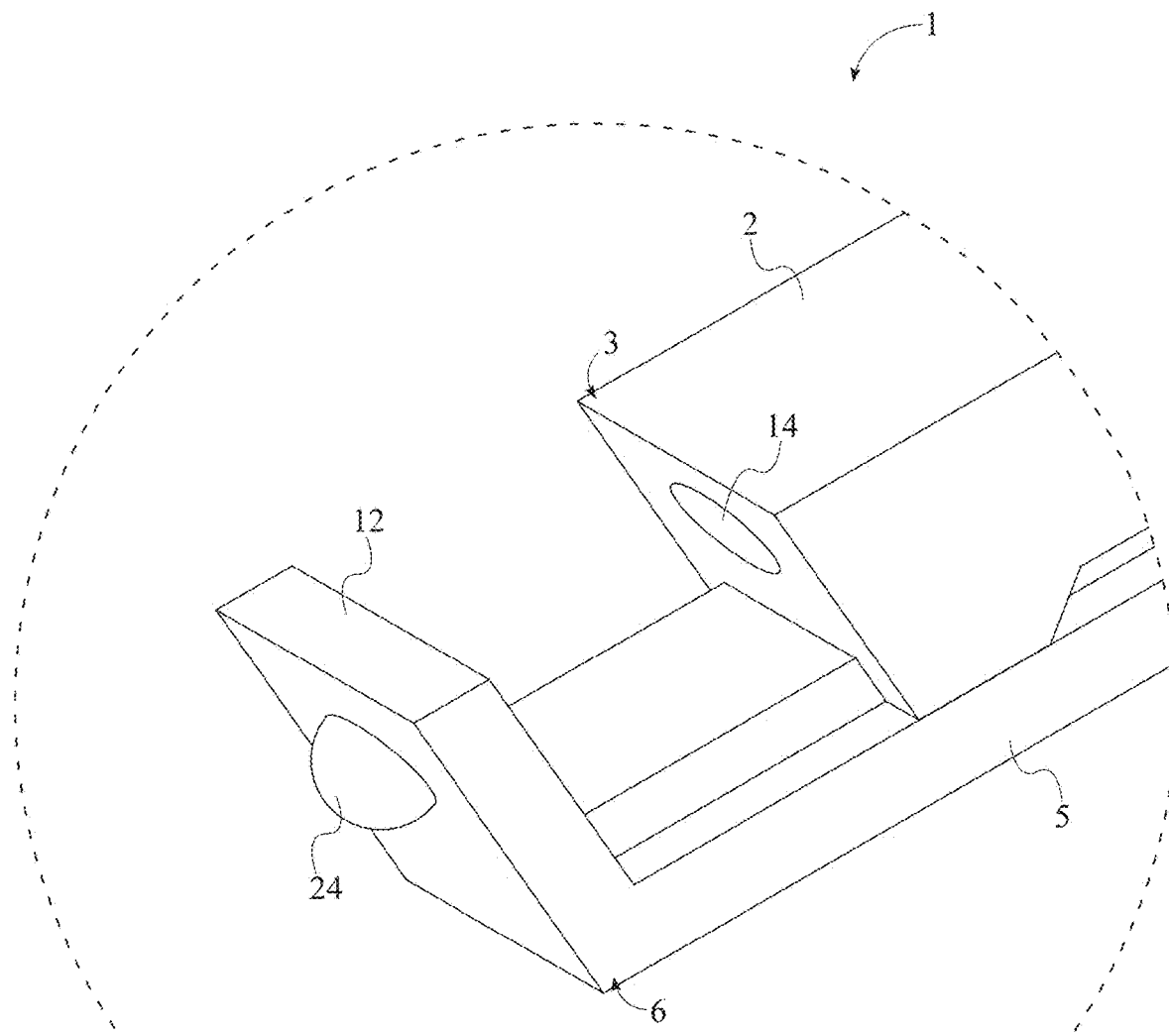
FIG. 2 is a magnified schematic view of the present invention, wherein the first tissue probe is shown on the cutting end of the present invention.
Figure 3:
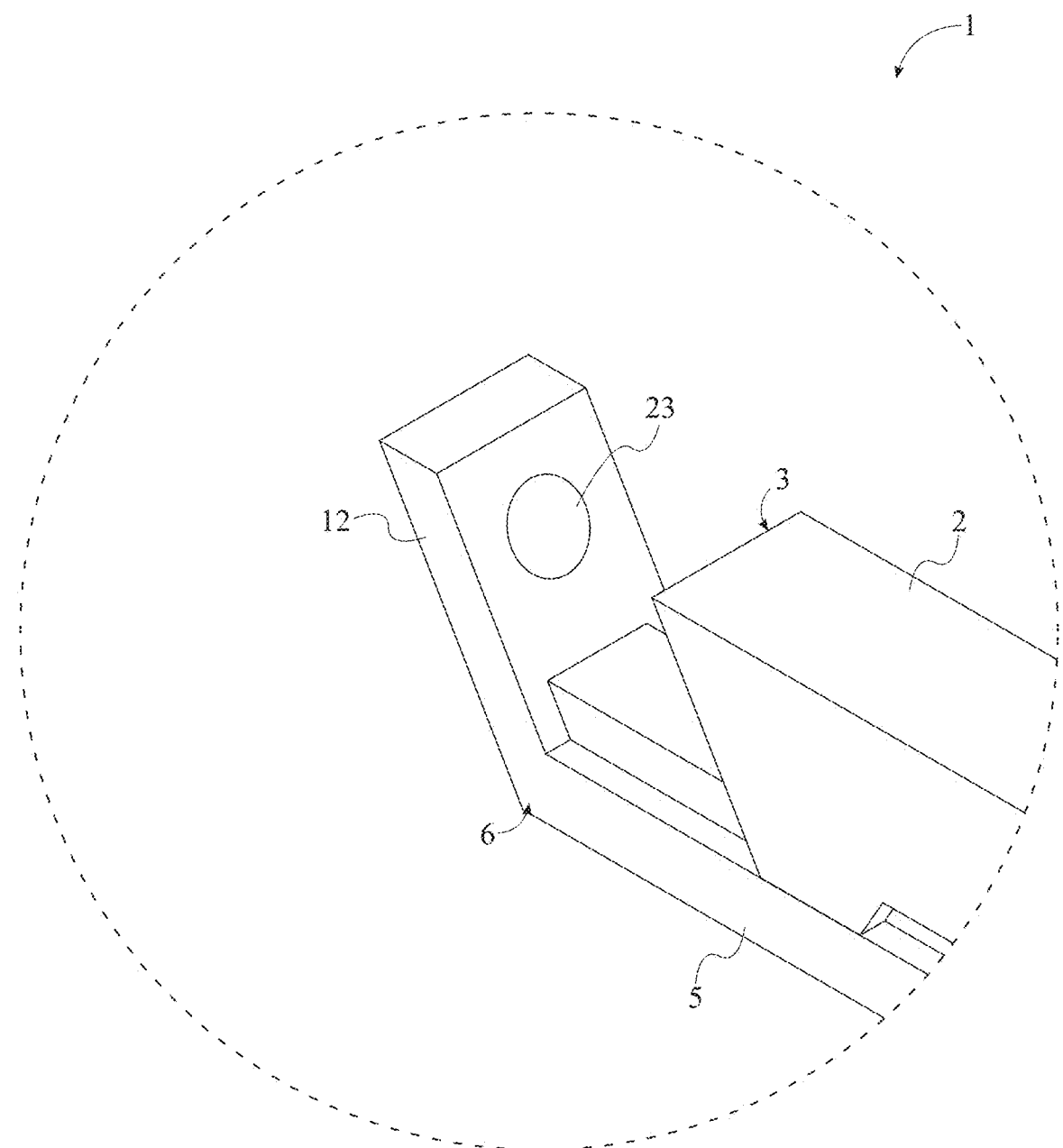
FIG. 3 is a magnified schematic view of the present invention, wherein the second tissue probe is shown on the footplate tip of the present invention.
Figure 4:
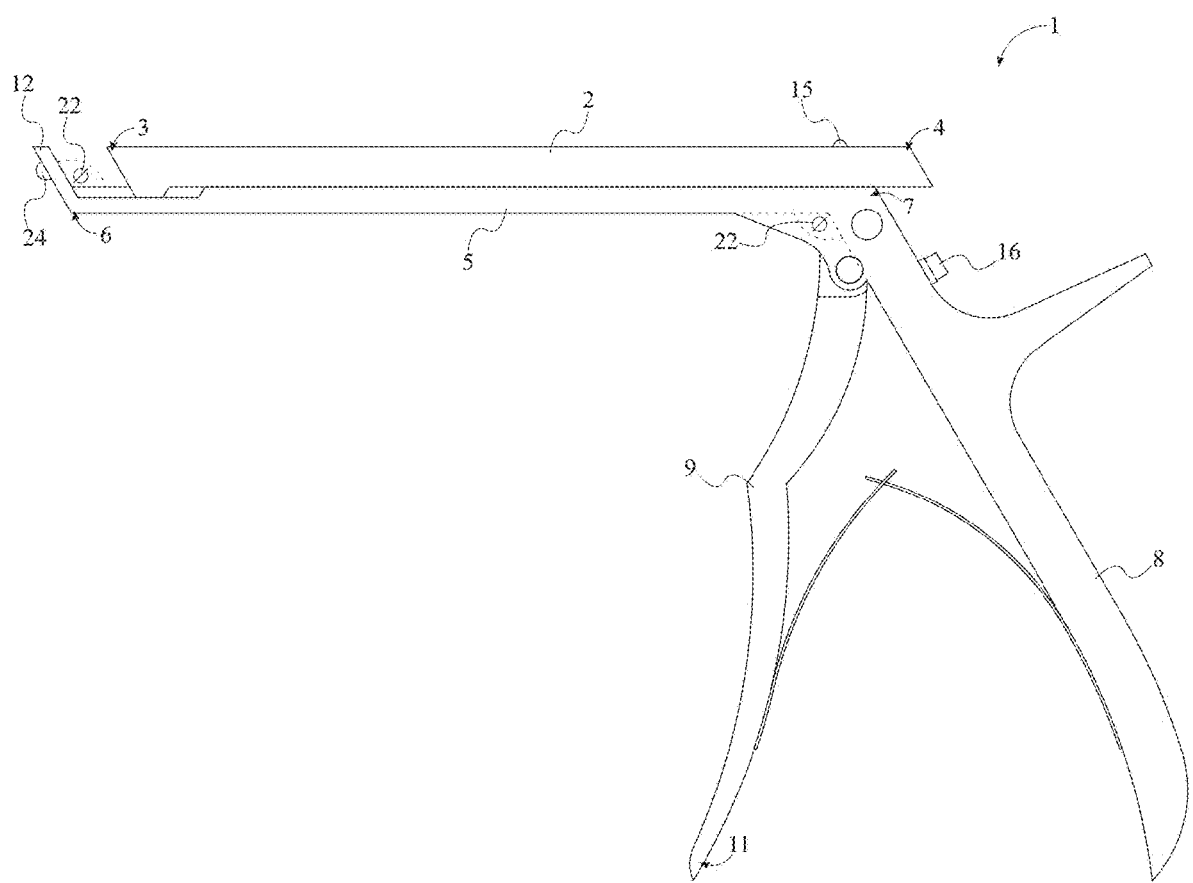
FIG. 4 is a side schematic view of the bone-and-tissue remover of the present invention, wherein the spring-loaded lever is shown disengaged.
Figure 5:
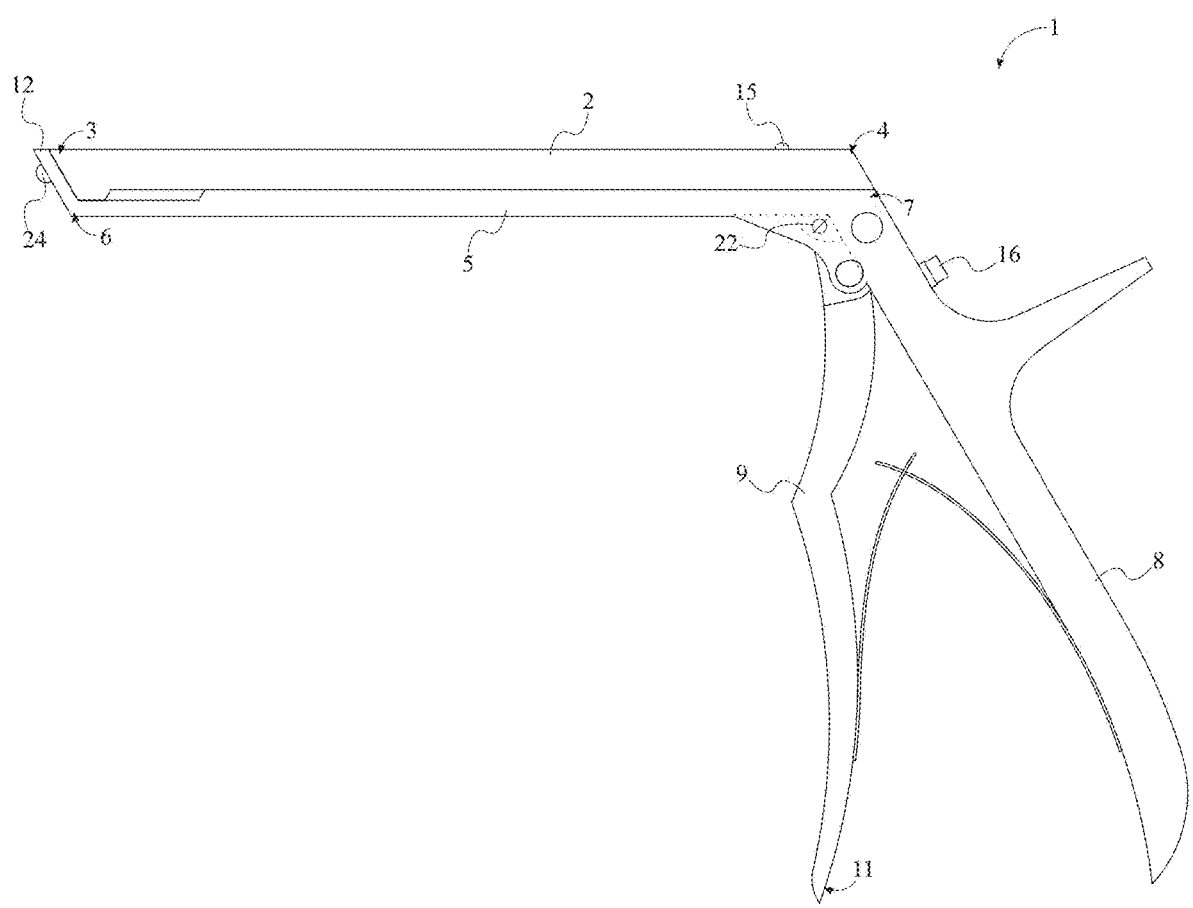
FIG. 5 is a side schematic view of the bone-and-tissue remover of the present invention, wherein the spring-loaded lever is shown engaged.
Figure 6:
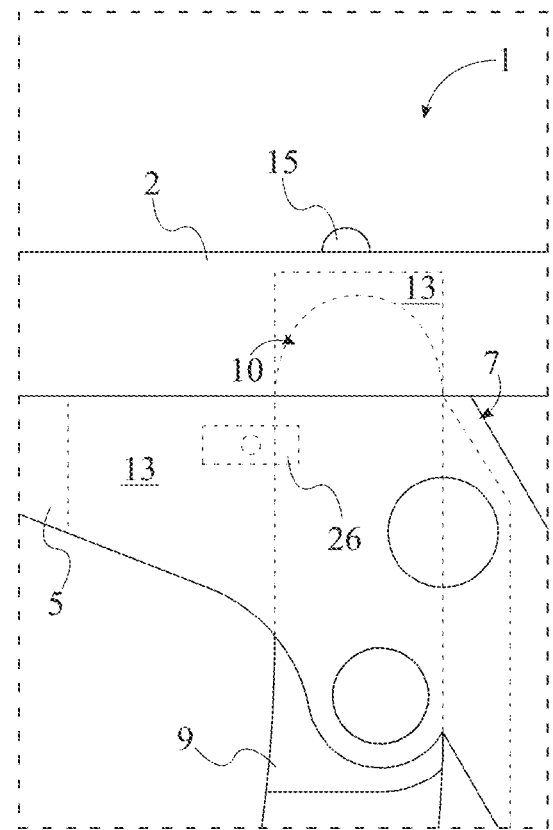
FIG. 6 is a magnified schematic view of the present invention, wherein the spring-loaded lever is shown disengaged.
Figure 7:
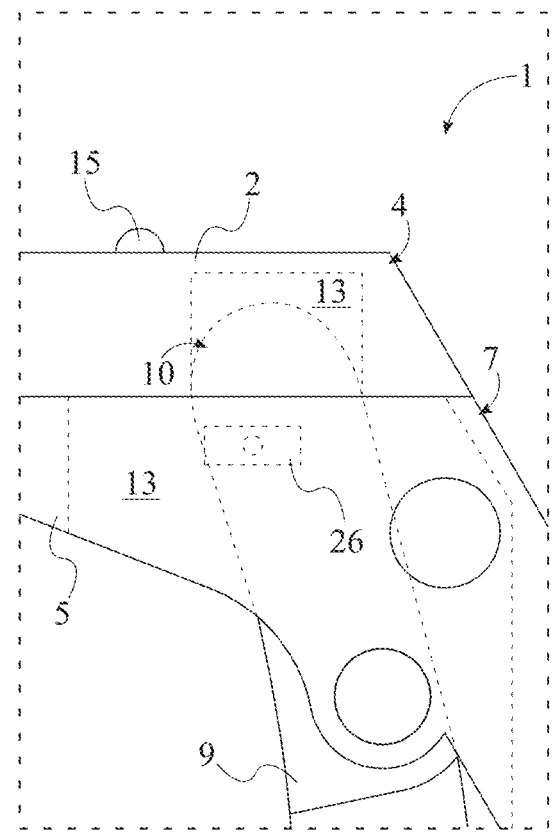
FIG. 7 is a magnified schematic view of the present invention, wherein the spring-loaded lever is shown engaged.

All illustrations of the drawings are for the purpose of describing selected versions of the present invention and are not intended to limit the scope of the present invention.

The present invention discloses a neuromonitoring surgical device for bone and tissue removal. The present invention is designed for spinal decompression procedures to enable the removal of bone or tissue while enabling the user to monitor the tissue being grasped with the device. As can be seen in FIG. 1 through 8, the present invention comprises a bone-and-tissue remover 1, a first tissue probe 14, a first light indicator 15, a cable connector 16, and a monitoring device 17. The bone-and-tissue remover 1 is designed to enable the minimal invasive removal of bone and/or tissue during the spinal decompression procedure. The first tissue probe 14 enables the automatic detection of neural tissue grasped by the bone-and-tissue remover 1. The first light indicator 15 directly alerts the user when neural tissue has been grasped, and or in the jaw of the device, by the bone-and-tissue remover 1. The cable connector 16 enables the electrical and electronic connection of the bone-and-tissue remover 1 to the monitoring device 17. The monitoring device 17 is a separate device that allows the user to monitor the operation of the first tissue probe 14 during the procedure. Further, the present invention can be connected universally to the preferred neuromonitoring system chosen by the surgical team and/or medical institution.

The general configuration of the aforementioned components enables the user to safely perform the spinal decompression procedure without accidentally resecting neural tissue. As can be seen in FIG. 1 through 8, the bone-and-tissue remover 1 is preferably designed to be utilized in a similar manner to the Kerrison Rongeurs. So, the bone-and-tissue remover 1 comprises an upper rail 2, a lower rail 5, a fixed handle 8, and a spring-loaded lever 9. The upper rail 2 and the lower rail 5 are elongated structures that enable the user to reach into the patient's body in a minimal invasive manner. The fixed handle 8 and the spring-loaded lever 9 correspond to the mechanism that allows the user to manually operate the bone-and-tissue remover 1. Further, the upper rail 2 comprises a cutting end 3 and a free end 4 corresponding to the terminal ends of the upper rail 2. In addition, the cutting end 3 corresponds to the structure that facilitates the resection of the target bone or tissue. Likewise, the lower rail 5 comprises a tip end 6 and a fixed end 7 corresponding to the terminal ends of the lower rail 5. The tip end 6 works in conjunction with the cutting end 3 to facilitate the resection of the target bone or tissue. Further, the bone-and-tissue remover 1 is preferably a disposable bone-and-tissue remover 1 that can be disposed of after use.

As can be seen in FIG. 1 through 8, the present invention can be arranged as follows: the upper rail 2 is positioned parallel to the lower rail 5 to form an overall rectangular structure. The cutting end 3 is positioned adjacent to the tip end 6, while the free end 4 is positioned adjacent to the fixed end 7. Further, the upper rail 2 is slidably mounted onto the lower rail 5 to secure the upper rail 2 to the lower rail 5 in such a manner that the upper rail 2 can slide along the lower rail 5. In addition, the fixed handle 8 is oriented at an obtuse angle 22 with the lower rail 5 to form an ergonomic structure that the user can comfortably grab onto. The fixed handle 8 is also terminally connected to the fixed end 7, opposite to the upper rail 2 to secure the fixed handle 8 to the lower rail 5 in a fixed manner. On the other hand, the spring-loaded lever 9 is hingedly connected to the lower rail 5, adjacent to the fixed handle 8, so that the user can engage the bone-and-tissue remover 1 manually. The spring-loaded lever 9 is operatively connected between the upper rail 2 to engage the bone-and-tissue remover 1 to cut the target bone or tissue. The spring-loaded lever 9 is used to move the cutting end 3 towards the tip end 6 when the spring-loaded lever 9 is pressed against the fixed handle 8. This way, when the target tissue is positioned between the tip end 6 and the cutting end 3, the user can press the spring-loaded lever 9 against the fixed handle 8 to press the target bone or tissue against the tip end 6 with the cutting end 3. The cutting end 3 is sharp enough to cut into the bone or tissue, and once cut, the bone or tissue is trapped within the cutting end 3 for safe retrieval.

As can be seen in FIG. 1 through 8, the first tissue probe 14 is also integrated into the cutting end 3 so that the first tissue probe 14 can generate electrical signals corresponding to the tissue being grasped between the tip end 6 and the cutting end 3. In addition, the first light indicator 15 is integrated into the upper rail 2, opposite to the lower rail 5, to visually alert the user of the type of tissue being detected using the first tissue probe 14. For example, the first light indicator 15 can be a Light Emitting Diode (LED) light that emits a green light when non-neural tissue is being grasped, and a red light when neural tissue is being grasped. Further, the cable connector 16 is integrated into the fixed handle 8, adjacent to the fixed end 7, to enable the connection of the bone-and-tissue remover 1 to the monitoring device 17. The monitoring device 17 can be a separate computing device that receives and processes the probe signal received from the first tissue probe 14 to determine the type of tissue being grasped. The monitoring device 17 is positioned offset to the bone-and-tissue remover 1 to not obstruct the surgical procedure. In the preferred embodiment, the monitoring device 17 is operated independently by any associated neuromonitoring company utilized during the surgical procedure with the use of the standard neuromonitoring technician with subsequent oversite by a remote neurologist per standardized protocol with utilization of intra operative neuromonitoring. Furthermore, the first tissue probe 14 and the first light indicator 15 are electronically and electrically connected to the monitoring device 17 via the cable connector 16. This way, the corresponding electronic signals are transmitted between the bone-and-tissue remover 1 and the monitoring device 17. For example, as the user grasps onto a tissue, the monitoring device 17 processes the probe signals received and relays the corresponding command signals that activate the first light indicator 15. In addition, the monitoring device 17 provides the power necessary for the operation of the first tissue probe 14 and the first light indicator 15.

As can be seen in FIG. 1 through 8, to facilitate the grasping of the desired tissue for resection, the bone-and-tissue remover 1 further comprise a footplate tip 12 that positions the grasped tissue against the cutting end 3. The footplate tip 12 is oriented at an obtuse angle 22 with the lower rail 5 to match the orientation of the cutting end 3. Further, the footplate tip 12 is terminally connected to the tip end 6, opposite to the fixed handle 8, to secure the footplate tip 12 to the lower rail 5. This way, the user can grasp onto the desired tissue by positioning the footplate tip 12 under the target tissue and then pressing the target tissue against the footplate tip 12 with the cutting end 3. Thus, the desired tissues is accurately resected.

To further ensure that the grasped tissue is not neural tissue, the present invention may further comprise a second tissue probe 23 that operates alongside the first tissue probe 14 to analyze the grasped tissue. As can be seen in FIG. 1 through 8, the second tissue probe 23 is integrated into the footplate tip 12 to secure the second tissue probe 23 to the footplate tip 12. In addition, the first tissue probe 14 is oriented towards the second tissue probe 23, and the second tissue probe 23 is oriented towards the first tissue probe 14. This way, the grasped tissue positioned in between the footplate tip 12 and the cutting end 3 is analyzed by the first tissue probe 14 and the second tissue probe 23 simultaneously. Furthermore, the second tissue probe 23 is electronically and electrically connected to the monitoring device 17 via the cable connector 16. This way, the probe signals of the second tissue probe 23 can be relayed to the monitoring device 17 along with the probe signals of the first tissue probe 14 for more accurate analysis of the grasped tissue. In other embodiments, additional probes can be implemented for more accurate analysis of the grasped tissue.

As can be seen in FIG. 1 through 8, to provide additional feedback to the user, the present invention may further comprise a second light indicator 24 that operates alongside the first light indicator 15 to alert the user when neural tissue has been grasped. Unlike the first light indicator 15, the second light indicator 24 is integrated into the footplate tip 12, opposite to the cutting end 3. This way, additional visual feedback is provided to the user during the procedure. Furthermore, the second light indicator 24 is electronically and electrically connected to the monitoring device 17 via the cable connector 16. Thus, the first light indicator 15 and the second light indicator 24 can emit the corresponding light signal depending on the analysis results of the monitoring device 17 corresponding to the tissue or bone being grasped.

As previously discussed, the bone-and-tissue remover 1 can be connected to the monitoring device 17 to enable the transmission of power and electric signals during the procedure between the components. As can be seen in FIG. 1 through 8, the present invention may further comprise a disposable power-and-data cable 25 that can be removably coupled between the cable connector 16 on the bone-and-tissue remover 1 and the monitoring device 17. The disposable power-and-data cable 25 can also be disposed of after use along with the bone-and-tissue remover 1. Further, the monitoring device 17 may comprise a controller 18, a power source 19, and a power-and-data port 20. The controller 18 corresponds to the computing unit of the monitoring device 17 capable of processing the probe signals received from the bone-and-tissue remover 1 and outputting accurate results. The power source 19 provides the power necessary for the operation of the monitoring device 17 and the bone-and-tissue remover 1. The power-and-data port 20 enable the coupling of the disposable power-and-data cable 25 to the monitoring device 17. So, the power-and-data port 20 is electronically connected to the controller 18 to relay the electronic signals from the tissue probes on the bone-and-tissue remover 1 to the controller 18 and to relay the command signals from the controller 18 to the light indicators on the bone-and-tissue remover 1. Further, the power-and-data port 20 and the controller 18 are electrically connected to the power source 19 to relay the power for the operation of the controller 18 and the electrical components on the bone-and-tissue remover 1. Furthermore, the cable connector 16 is electronically and electrically connected to the power-and-data port 20 via the disposable power-and-data cable 25 to enable the coupling of the bone-and-tissue remover 1 to the monitoring device 17 for remote monitoring during the procedure.

Figure 8:
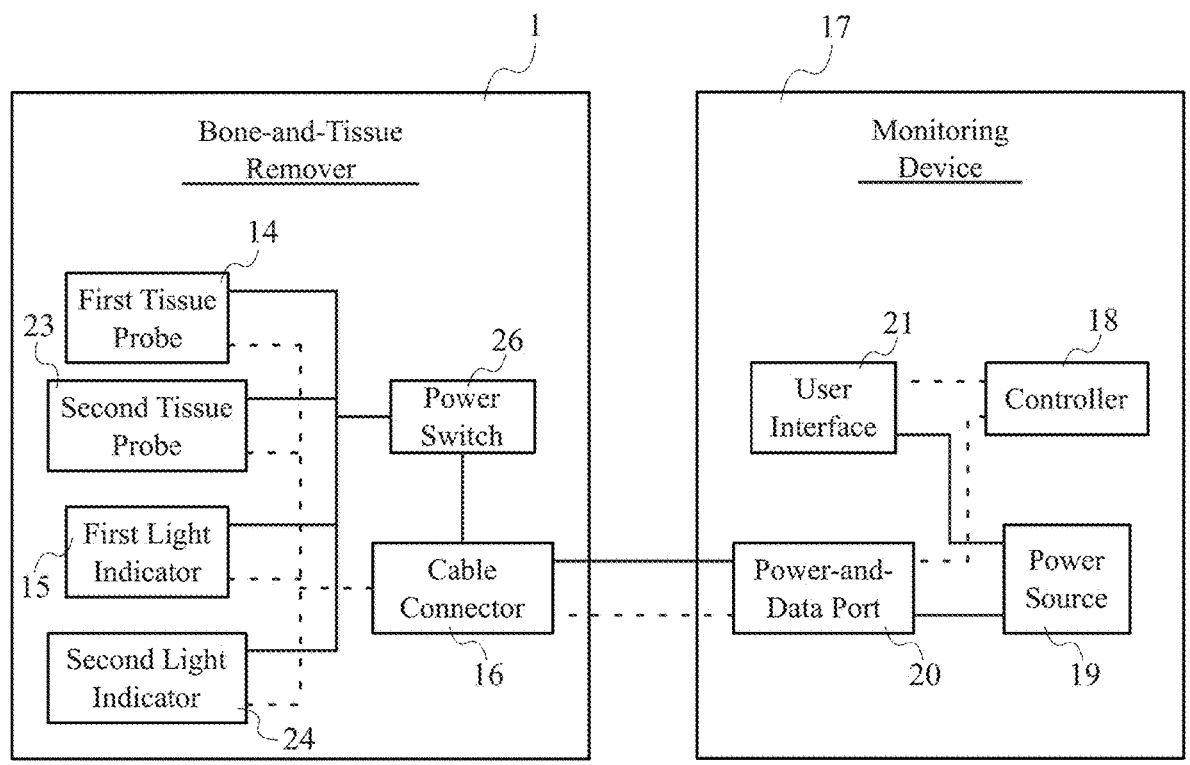
FIG. 8 is a block diagram showing the electrical connections and the electronic connections of the present invention, wherein the electrical connections are shown in solid lines, and wherein the electronic connections are shown in dashed lines.

As can be seen in FIG. 8, the monitoring device 17 may further comprise a user interface 21 that enables the user to interact with the monitoring device 17 during the procedure. For example, the user interface 21 may include an input device such as a physical or digital keyboard for the user to configure the operation of the monitoring device 17. The user interface 21 may also include a display that outputs the probe signals and the corresponding analysis results to help the user monitor the tissue being grasped with the bone-and-tissue remover 1. So, the user interface 21 is electronically connected to the controller 18 to enable the transmission of the corresponding electronic signals between the user interface 21 and the controller 18. Further, the user interface 21 is electrically connected to the power source 19 to provide the user interface 21 with the power necessary for operation. In other embodiments, the monitoring device 17 may include additional features that provide greater control to the user of the monitoring process during the surgical procedure.

As previously discussed, the user can engage the bone-and-tissue remover 1 by manually engaging the spring-loaded lever 9. As can be seen in FIG. 1 through 7, in some embodiments, the bone-and-tissue remover 1 may further comprise a lever channel 13 that allows the spring-loaded lever 9 to engage the upper rail 2. In addition, the spring-loaded lever 9 may comprise a first lever end 10 and a second lever end 11 corresponding to the terminal ends of the spring-loaded lever 9. So, the lever channel 13 traverses through the lower rail 5 and into the upper rail 2, adjacent to the fixed handle 8, to provide a space that enables the spring-loaded lever 9 to engage with the upper rail 2 through the lower rail 5. In addition, the first lever end 10 is positioned opposite to the second lever end 11 along the spring-loaded lever 9 due to the elongated shape of the spring-loaded lever 9. Further, the spring-loaded lever 9 is hingedly connected to the lower rail 5, adjacent to the first lever end 10, which frees the first lever end 10 to engage with the upper rail 2. Furthermore, the first lever end 10 is positioned within the lever channel 13 so that first lever end 10 physically engages the upper rail 2.

As can be seen in FIG. 1 through 7, this embodiment of the spring-loaded lever 9 enables the user to manually operate the bone-and-tissue remover 1 in the following manner: when not in use, the spring-loaded lever 9 is separated from the fixed handle 8 by the corresponding spring mechanism. The first lever end 10 keeps the upper rail 2 in a position where the cutting end 3 is offset to the tip end 6 to leave a space that accommodates the target tissue. The spring mechanism can be two leaf spring interconnected in between the spring-loaded lever 9 and the fixed handle 8. During the procedure, the user can move the bone-and-tissue remover 1 by grabbing onto the spring-loaded lever 9 and the fixed handle 8 without pressing onto the spring-loaded lever 9. Once the target tissue has been grasped and the light indicators show that the grasped tissue is not neural tissue, the user can press the spring-loaded lever 9 against the fixed handle 8.

As can be seen in FIG. 1 through 7, when the user presses on the spring-loaded lever 9, the spring-loaded lever 9 pivots about the hinge connection that cause the first lever end 10 to rotate towards the tip end 6. As the first lever end 10 rotates towards the tip end 6, the first lever end 10 moves the upper rail 2 in the same direction, which in turn moves the cutting edge towards the tip end 6. As the grasped tissue is pressed in between the footplate tip 12 and the cutting edge, the grasped tissue is cut by the cutting edge, and the cut tissue is retained in between the cutting end 3 and the tip end 6. In some embodiments, the present invention may further comprise a locking mechanism integrated into the lower rail 5 that locks the cutting end 3 and the tip end 6 in position. The locking mechanism can be connected in between the lower rail 5 and the spring-loaded lever 9 in such a way that the user can engage the locking mechanism to lock the cutting end 3 in position against the tip end 6 once the target tissue has been resected. This way, the user can safely retrieve the resected tissue when removing the bone-and-tissue remover 1 from the patient's body. In other embodiments, additional features can be implemented that facilitate the resection of bone or tissue in a minimally intrusive manner.

In general, the tissue probes and the light indicators remain activated as long as the bone-and-tissue remover 1 is connected to the monitoring device 17. This way, the tissue probes and the light indicators deactivate only when the user disconnects the bone-and-tissue remover 1 from the monitoring device 17. As can be seen in FIG. 1 through 8, in some embodiments, the present invention may further comprise a power switch 26 that activates the tissue probes and the light indicators only when the user engages the spring-loaded lever 9. To do so, the power switch 26 is mounted within the lever channel 13, adjacent to the first lever end 10, to secure the power switch 26 within the lower rail 5. The power switch 26 is arranged so that when the spring-loaded lever 9 is engaged, the rotating first lever end 10 engages the power switch 26 to activate the tissue probes and the light indicators. Further, the first tissue probe 14, the second tissue probe 23, the first light indicator 15, and the second light indicator 24 are electrically connected to the cable connector 16 via the power switch 26. In other embodiments, the power switch 26 can be externally integrated into the fixed handle 8 so that the user can manually activate the tissue probes and the light indicators when desired.

Although the invention has been explained in relation to its preferred embodiment, it is to be understood that many other possible modifications and variations can be made without departing from the spirit and scope of the invention.

What is claimed is:

1. A neuromonitoring surgical system for bone and tissue removal comprising:
 a bone-and-tissue remover;
 a first tissue probe;
 a first light indicator;
 a cable connector;
 a monitoring device;
 the bone-and-tissue remover comprising an upper rail, a lower rail, a fixed handle, a spring-loaded lever, and a lever channel;
 the upper rail comprising a cutting end and a free end;
 the lower rail comprising a tip end and a fixed end;
 the upper rail being positioned parallel to the lower rail;
 the cutting end being positioned adjacent to the tip end;
 the upper rail being slidably mounted onto the lower rail;
 the fixed handle being oriented at an obtuse angle with the lower rail;
 the fixed handle being terminally connected to the fixed end, opposite to the upper rail;
 the lever channel traversing through the lower rail and into the upper rail, adjacent to the fixed handle;
 the spring-loaded lever being hingedly connected to the lower rail, adjacent to the fixed handle;
 the spring-loaded lever being operatively connected to the upper rail via the lever channel, wherein the spring-loaded lever is used to move the cutting end towards the tip end when the spring-loaded lever is pressed against the fixed handle;
 the first tissue probe being integrated into the cutting end;
 the first light indicator being integrated into the upper rail, opposite to the lower rail;
 the cable connector being integrated into the fixed handle, adjacent to the fixed end;
 the monitoring device being positioned offset to the bone-and-tissue remover; and
 the first tissue probe and the first light indicator being electronically and electrically connected to the monitoring device via the cable connector.

2. The neuromonitoring surgical system for bone and tissue removal as claimed in claim 1, wherein the bone-and-tissue remover is a disposable bone-and-tissue remover.

3. The neuromonitoring surgical system for bone and tissue removal as claimed in claim 1 further comprising:
 the bone-and-tissue remover further comprising a footplate tip;
 the footplate tip being oriented at an obtuse angle with the lower rail; and
 the footplate tip being terminally connected to the tip end, opposite to the fixed handle.

4. The neuromonitoring surgical system for bone and tissue removal as claimed in claim 3 further comprising:
 a second tissue probe;
 the second tissue probe being integrated into the footplate tip;
 the first tissue probe being oriented towards the second tissue probe;
 the second tissue probe being oriented towards the first tissue probe; and
 the second tissue probe being electronically and electrically connected to the monitoring device via the cable connector.

5. The neuromonitoring surgical system for bone and tissue removal as claimed in claim 3 further comprising:
 a second light indicator;
 the second light indicator being integrated into the footplate tip, opposite to the cutting end; and
 the second light indicator being electronically and electrically connected to the monitoring device via the cable connector.

6. The neuromonitoring surgical system for bone and tissue removal as claimed in claim 1 further comprising:
 a disposable power-and-data cable;
 the monitoring device comprising a controller, a power source, and a power-and-data port;
 the power-and-data port being electronically connected to the controller;
 the power-and-data port and the controller being electrically connected to the power source; and
 the cable connector being electronically and electrically connected to the power-and-data port via the disposable power-and-data cable.

7. The neuromonitoring surgical system for bone and tissue removal as claimed in claim 6 further comprising:
 the monitoring device further comprising a user interface;
 the user interface being electronically connected to the controller; and
 the user interface being electrically connected to the power source.

8. The neuromonitoring surgical device-system for bone and tissue removal as claimed in claim 1 further comprising:
 the spring-loaded lever comprising a first lever end and a second lever end;
 the first lever end being positioned opposite to the second lever end along the spring-loaded lever;
 the spring-loaded lever being hingedly connected to the lower rail, adjacent to the first lever end; and
 the first lever end being positioned within the lever channel.

9. The neuromonitoring surgical system for bone and tissue removal as claimed in claim 8 further comprising:
 a power switch;
 the power switch being mounted within the lever channel, adjacent to the first lever end; and
 the first tissue probe and the first light indicator being electrically connected to the cable connector via the power switch.

10. A neuromonitoring surgical system for bone and tissue removal comprising:
 a disposable bone-and-tissue remover;
 a first tissue probe;
 a first light indicator;
 a cable connector;
 a monitoring device;
 the disposable bone-and-tissue remover comprising an upper rail, a lower rail, a fixed handle, a spring-loaded lever, a lever channel, and a footplate tip;
 the upper rail comprising a cutting end and a free end;
 the lower rail comprising a tip end and a fixed end;
 the upper rail being positioned parallel to the lower rail;
 the cutting end being positioned adjacent to the tip end;
 the upper rail being slidably mounted onto the lower rail;
 the fixed handle being oriented at an obtuse angle with the lower rail;

the fixed handle being terminally connected to the fixed end, opposite to the upper rail;

the lever channel traversing through the lower rail and into the upper rail, adjacent to the fixed handle;

the spring-loaded lever being hingedly connected to the lower rail, adjacent to the fixed handle;

the spring-loaded lever being operatively connected to the upper rail via the lever channel, wherein the spring-loaded lever is used to move the cutting end towards the tip end when the spring-loaded lever is pressed against the fixed handle;

the footplate tip being oriented at an obtuse angle with the lower rail;

the footplate tip being terminally connected to the tip end, opposite to the fixed handle;

the first tissue probe being integrated into the cutting end;

the first light indicator being integrated into the upper rail, opposite to the lower rail;

the cable connector being integrated into the fixed handle, adjacent to the fixed end;

the monitoring device being positioned offset to the bone-and-tissue remover; and the first tissue probe and the first light indicator being electronically and electrically connected to the monitoring device via the cable connector.

11. The neuromonitoring surgical system for bone and tissue removal as claimed in claim 10 further comprising:
a second tissue probe;
the second tissue probe being integrated into the footplate tip;
the first tissue probe being oriented towards the second tissue probe;
the second tissue probe being oriented towards the first tissue probe; and
the second tissue probe being electronically and electrically connected to the monitoring device via the cable connector.

12. The neuromonitoring surgical system for bone and tissue removal as claimed in claim 10 further comprising:
a second light indicator;
the second light indicator being integrated into the footplate tip, opposite to the cutting end; and
the second light indicator being electronically and electrically connected to the monitoring device via the cable connector.

13. The neuromonitoring surgical system for bone and tissue removal as claimed in claim 10 further comprising:
a disposable power-and-data cable;
the monitoring device comprising a controller, a power source, a power-and-data port, and a user interface;
the power-and-data port and the user interface being electronically connected to the controller;
the power-and-data port, the user interface, and the controller being electrically connected to the power source; and
the cable connector being electronically and electrically connected to the power-and-data port via the disposable power-and-data cable.

14. The neuromonitoring surgical system for bone and tissue removal as claimed in claim 10 further comprising:
the spring-loaded lever comprising a first lever end and a second lever end;
the first lever end being positioned opposite to the second lever end along the spring-loaded lever;
the spring-loaded lever being hingedly connected to the lower rail, adjacent to the first lever end; and
the first lever end being positioned within the lever channel.

15. The neuromonitoring surgical system for bone and tissue removal as claimed in claim 14 further comprising:
a power switch;
the power switch being mounted within the lever channel, adjacent to the first lever end; and
the first tissue probe and the first light indicator being electrically connected to the cable connector via the power switch.

16. A neuromonitoring surgical system for bone and tissue removal comprising:
a disposable bone-and-tissue remover;
a first tissue probe;
a first light indicator;
a cable connector;
a monitoring device;
the disposable bone-and-tissue remover comprising an upper rail, a lower rail, a fixed handle, a spring-loaded lever, a lever channel, and a footplate tip;
the upper rail comprising a cutting end and a free end;
the lower rail comprising a tip end and a fixed end;
the upper rail being positioned parallel to the lower rail;
the cutting end being positioned adjacent to the tip end;
the upper rail being slidably mounted onto the lower rail;
the fixed handle being oriented at an obtuse angle with the lower rail;
the fixed handle being terminally connected to the fixed end, opposite to the upper rail;
the lever channel traversing through the lower rail and into the upper rail, adjacent to the fixed handle;
the spring-loaded lever being hingedly connected to the lower rail, adjacent to the fixed handle;
the spring-loaded lever being operatively connected to the upper rail via the lever channel, wherein the spring-loaded lever is used to move the cutting end towards the tip end when the spring-loaded lever is pressed against the fixed handle;
the footplate tip being oriented at an obtuse angle with the lower rail;
the footplate tip being terminally connected to the tip end, opposite to the fixed handle;
the first tissue probe being integrated into the cutting end;
the first light indicator being integrated into the upper rail, opposite to the lower rail;
the cable connector being integrated into the fixed handle, adjacent to the fixed end;
the monitoring device being positioned offset to the bone-and-tissue remover; and
the first tissue probe and the first light indicator being electronically and electrically connected to the monitoring device via the cable connector.

17. The neuromonitoring surgical system for bone and tissue removal as claimed in claim 16 further comprising:
a second tissue probe;
the second tissue probe being integrated into the footplate tip;
the first tissue probe being oriented towards the second tissue probe;
the second tissue probe being oriented towards the first tissue probe; and
the second tissue probe being electronically and electrically connected to the monitoring device via the cable connector.

18. The neuromonitoring surgical system for bone and tissue removal as claimed in claim 16 further comprising:
a second light indicator;

the second light indicator being integrated into the footplate tip, opposite to the cutting end; and the second light indicator being electronically and electrically connected to the monitoring device via the cable connector.

19. The neuromonitoring surgical system for bone and tissue removal as claimed in claim 16 further comprising:

a disposable power-and-data cable;

the monitoring device comprising a controller, a power source, a power-and- data port, and a user interface;

the power-and-data port and the user interface being electronically connected to the controller;

the power-and-data port, the user interface, and the controller being electrically connected to the power source; and the cable connector being electronically and electrically connected to the power-and-data port via the disposable power-and-data cable.

20. The neuromonitoring surgical system for bone and tissue removal as claimed in claim 16 further comprising:

a power switch;

the spring-loaded lever comprising a first lever end and a second lever end;

the first lever end being positioned opposite to the second lever end along the spring-loaded lever;

the spring-loaded lever being hingedly connected to the lower rail, adjacent to the first lever end;

the first lever end being positioned within the lever channel;

the power switch being mounted within the lever channel, adjacent to the first lever end; and the first tissue probe and the first light indicator being electrically connected to the cable connector via the power switch.

* * * * *